United States Patent [19]

Wright et al.

[11] Patent Number: 5,772,583
[45] Date of Patent: Jun. 30, 1998

[54] STERNAL RETRACTOR WITH ATTACHMENTS FOR MITRAL & TRICUSPID VALVE REPAIR

[76] Inventors: John T. M. Wright, 555 S. Downing St., Denver, Colo. 80209; Donald P. Elliott, 5401 E. Dakota Ave, #12, Denver, Colo. 80222; Francis C. Wells, 40 West Street, Great Gransden, Sandy, Befordshire SG193AU, England

[21] Appl. No.: 581,035

[22] Filed: Dec. 29, 1995

Related U.S. Application Data

[63] Continuation-in-part of Ser. No. 184,511, Jan. 21, 1994, abandoned.

[51] Int. Cl.⁶ .................................. A61B 1/30; B25G 3/36
[52] U.S. Cl. .................... 600/232; 600/215; 600/234; 600/235; 403/389
[58] Field of Search ................................... 600/201, 215, 600/226–228, 231, 232, 234, 235; 606/190, 191, 198; 403/400, 384, 389, 396; 269/37

[56] References Cited

U.S. PATENT DOCUMENTS

1,950,635  3/1934  Steinmayer .......................... 403/400
4,627,421  12/1986  Symbas et al. ....................... 600/232
4,726,356  2/1988  Santilli et al. ........................ 600/232
4,852,552  8/1989  Chaux .................................. 600/232
4,865,019  9/1989  Phillips ................................ 600/232
4,989,587  2/1991  Farley .................................. 600/232
5,025,780  6/1991  Farley ............................... 403/389 X
5,052,373  10/1991  Michelson ....................... 600/232 X
5,088,472  2/1992  Fakhrai ................................ 600/214
5,167,223  12/1992  Koros et al. ......................... 600/232
5,242,240  9/1993  Gorham ............................ 403/389 X

*Primary Examiner*—John P. Leubecker

[57] ABSTRACT

A sternal retractor for applying an opening force evenly along the respective edges of a patient's sternum during heart surgery comprises a curved rack having a length, a width, and a thickness, wherein the rack is curved in the thickness direction, hinged arms mounted to the rack, a cog mechanism for forcing one of the arms to move along the rack, and retractor blades pivotally mounted to the arms. An atrial retractor which are used to retract the left and right atrium connects to an arm of the sternal retractor by an H-shaped mounting rod assembly. The assembly comprises two elongated rods mounted in spaced parallel relationship by a clamp proximate the center of the rods. A ball clamp associated with the sternal retractor and atrial retractor comprises locking discoid blocks for releasably interconnecting a plurality of rods together.

15 Claims, 6 Drawing Sheets

STERNAL RETRACTOR WITH ATTACHMENTS FOR MITRAL & TRICUSPID VALVE REPAIR

CROSS-REFERENCE TO RELATED APPLICATION

This is a continuation-in-part of co-pending U.S. patent application No. 08/184,511, Filed Jan. 21, 1994, to be abandoned, to which priority is claimed.

BACKGROUND OF THE INVENTION

This invention relates to an improved sternal retractor for use in open heart surgery, with an attachable mechanism (which may be adapted to certain other commercially available sternal retractors) to aid in the exposure of the mitral, aortic or tricuspid valve. Such exposure is desirable when carrying out surgical repairs or replacement procedures on said valves.

Surgery of the heart is a common surgical procedure and about 600,000 are currently performed in the worldwide each year, of which about half take place in the U.S. Most heart operations involve coronary artery bypass grafting, but a significant number involve heart valve replacement or repair, including replacement or valvuloplasty of mitral and tricuspid valves. This surgical technique requires adequate exposure of the valve annulus. Good exposure of the mitral valve is a difficult problem in some patients due to individual anatomy. The heart is usually exposed by a sternal midline incision. Following the opening of the sternum a sternal retractor is used to open the sternum a distance of several inches.

Sternal retractors have been in use for many years. The following patents and publication describe typical devices.

| U.S. Pat. No. 2,564,118 | 08/1951 | Mahorner |
| U.S. Pat. No. 4,627,421 | 12/1986 | Symbas et al. |
| U.S. Pat. No. 4,726,356 | 2/1988 | Santilli et al. |
| U.S. Pat. No. 4,852,552 | 8/1989 | Chaux |
| U.S. Pat. No. 4,865,019 | 9/1989 | Phillips |
| U.S. Pat. No. 4,989,587 | 2/1991 | Farley |
| U.S. Pat. No. 5,088,472 | 2/1992 | Fakhrai |
| U.S. Pat. No. 5,167,223 | 12/1992 | Koros |

Publication-Fehling Medical AG brochure

In general, the typical retractor consists of two sternal blades attached, respectively, to a pair of arms. One arm is rigidly attached to a rack containing a single row of gear teeth, and the second arm rigidly fixed to a moving member that is able to slide along the rack. A rotatable handle, hinged to a simple cog gear is contained in the moving member and engages the rack. Rotation of the handle caused the member to move along the rack, thus changing the separation distance between the sternal blades.

While surgical retractors, in general, perform the same function—spreading apart two adjacent anatomical structures to permit access by the surgeon—the requirements for a satisfactory retractors for one purpose differ greatly from requirements for a retractor intended for a different surgical procedure. Thus, there is no basis for extrapolating a function, structure or concept from one kind of retractor to another kind of retractor. A rib cage retractor, or a back retractor, for example, teaches little of any value or relevance with respect to a sternal retractor or a jaw retractor.

With respect to a sternal retractor, for example, the blades force the sternum to open in a parallel manner have been found to be unsatisfactory because the sternum has a marked tendency to open further at the xiphoid appendix than at the manubrium, a localized pressure point is generated near the manubrium which may be sufficient to cause localized sternal or first rib fracture. Nothing in the art of back or jaw retractors, however, bears upon the requirements of a fully satisfactory sternal retractor.

The straight rack of the conventional retractor forces the cut edges of the sternum to open in a linear manner. However, because ribs articulate with both the vertebrae and the costal cartilages of the sternum, the natural tendency of the sternum is to open along a curved path (of a radius curvature of approximately 7 inches as measured from several male patients from CAT scans). The forces imposed by a straight rack configuration probably cause excessive movement of the costal cartilages probably adding to post-operative pain and discomfort in breathing. From the surgeons point of view, the lateral protrusion of the linear rack along the patients abdomen (or neck, depending upon how the retractor is used) sometimes interferes with the surgeon.

Two atrial retractor attachments are available for conventional sternal retractors. The first is the Carpentier retractor, which uses a series of square holes in the atrial retractor blades to engage with "L" shaped protrusions on its accompanying sternal retractor. This arrangement is quite inconvenient to the surgeon, has poor versatility in terms of adjustability, and the protrusions have a marked tendency to catch sutures. It is considered to be a poor device by some surgeons who have used it. The second is the atrial retractor described in U.S. Pat. No. 4,627,421. This is a versatile atrial retractor that is hampered by a mechanical design that has caused the device to malfunction due to slippage after prolonged use. This is because the clamp means relies on the tightening of a horseshoe shaped piece around a rod. To achieve adequate bending a compromise has to be made between the force required to bend the devise in the required area and the cross-sectional area of the metal at the apex of the curve of the horseshoe shape. Over tightening in use causes permanent stretching at this point, the clamping force reduced, more over tightening is used to attempt to produced a tight clamp, which then fails to hold. The attachment also has the disadvantage that it has multiple protuberances that can interfere with cardiovascular sutures. It also requires a bar attachment that is permanently attached to the sternal retractor that can interfere with cardiovascular sutures. This invention overcomes these problems.

Fakhrai, U.S. Pat. No. 5,088,472, addressed the problem with straight retractors arising from the fact that the sternum has a tendency to open further at the xiphoid appendix than at the manubrium. Fakhrai discloses a retractor with a flat, i.e. mono-planar, rack, as part of a relatively standard rack and pinion mechanism, which is arcuate perpendicular to the plane in which the rack lies. This defines a single, fixed angle between the sternum engagement blades. This is a partial solution to the problem.

Koros, U.S. Pat. No. 5,167,223, provides a variation of the traditional single blade sternum engaging means by providing two separately pivoted engagement blades secured on the retractor arms. This approach permits localized adaptation at the point of engagement of the blades with the sternum. Each of the blades moves outwardly in a straight path and, therefore, does not accommodate to the nonparallel separation of the sternum during retraction. The main advantage of the two-blade system of Koros is, apparently, reduction of the degree of stress at any one point by providing more points of engagement with the sternum.

It is an objective of this invention to provide an sternal retractor that will allow the split sternum to open such that the cut edges are not parallel in the anterior-posterior plane.

It is a further objective of this invention to provide an sternal retractor that will allow the split sternum to open such that the cut edges may pivot around the rib-spine joints.

It is a further objective of this invention to provide attachments to sternal retractors that allow the surgeon easily to position and retain the atrial retractor blade to retract the left and right atrium to allow adequate exposure of the mitral and tricuspid valves.

Other objectives and advantages of this invention will be more apparent from the detailed description of the device which follows.

SUMMARY OF THE INVENTION

This invention relates to a sternal retractor with attachments for retracting the left or right atrium. The sternal retractor has pivoting sternal blade that are free to rotate ±10° which allow a more natural opening of the chest, which should significantly reduced the incidence of complication due to sternal fracture. The rack of the retractor has a downward curve of 10" radius of curvature, and the arms or the retractor have inclined hinges. The curved rack of the sternal retractor, combined with the hinged arms, allows more natural opening of the chest whilst not obstructing the surgeon work area. A measuring scale on the rack helps prevent over extension of the sternum.

The atrial retracting attachment consist of one or more atrial retractor blades, a pillar clamp, one or two mounting rods and one or more ball clamp clamps. The pillar clamp has protruding dowel pins on the lower face which engage in corresponding recesses in the sternal retractor arms. When the clamp screw is tightened the pillar is firmly fixed to the sternal retractor, and the mounting bar firmly held in place by means of the half collet. A mounting rod may be affixed to one or other arm of the sternal retractor by means of the pillar clamp. A ball clamp is used to clamp an atrial retractor to the mounting bar, or one mounting bar to another. The ball clamp has a single clamp screw that when tightened closes two half collets. Conversely, when the clamp screw is slackened, the upper and lower portions are free to rotate with respect to one another, and the rods of the mounting bar and atrial retractors are free to slide and rotate in their respective holes. Tightening of the clamp screw with the hexagonal "Tee" wrench provided locks the device and prevents all movement. This mechanical design ensures firm reliable fixation of the atrial retractors, after repeated use.

In use the atrial retractor blades rakes are infinitely adjustable in terms of angulation, position and rotation. The atrial retractor components are easily attached and detachable from the sternal retractor. Adequate exposure of the mitral or tricuspid valve may be achieved by using one, two or three atrial retractor blades. The components do not interfere with implanting or bypass grafting sutures, and when the atrial retractor is removed, the sternal retractor has no protrusions that can interfere with cardiovascular sutures.

The improved sternal and atrial retractor has the following benefits to the patient:

1) The new design provides sternal blade that pivot to allow differential opening between the nyobial any zyphoidal ends of the sternal incision that allow the split sternum to open such that the cut edges are not parallel in the anterior-posterior plane. This feature minimizes the complication of sternal fracture.

2) The sternal separation scale on the rack serves to remind the surgeon to avoid over extension of the sternum, also minimizing the complication of sternal fracture.

3) The new design provides an sternal retractor that will allow the split sternum to open such that the ribs will more normally articulate at the rib head-vertebrae joint without over extension of the costal cartilages. This should reduce postoperative discomfort.

4) The greatly improved exposure of the mitral or tricuspid valve results in a greater likelihood in the valve being successfully repaired, rather than being replaced, with resulting long term benefit to the patient.

5) The incorporation of an "H" mounting bar permits greater adjustment of retractor rods and hooks for providing access the patient's heart, lungs and related organs.

The present invention is embodied in a sternal retractor. The sternal retractor comprises a curved rack having a first end and a second end, a first arm attached adjacent the first end, a second arm mounted for movement along the length of the rack between the first and second ends. In a preferred form, the first arm comprises a mount which has a rectangular passage formed therethrough to accept the rack. Also in a preferred form, a first articulated arm is pivotally secured to the mount, and the second arm comprises a mounting body through which is formed a passage having a generally rectangular cross-section to receive the rack, the passage being sufficiently larger than the rack to permit the body to slide along the rack. In the exemplary embodiment, an aperture is formed through the body perpendicular to the passage and a cog mechanism extends through the aperture. The cog mechanism comprises an upstanding pivot mount, an actuating handle connected thereto, a flange supporting the pivot mount and resting the surface of the body circumferentially adjacent the aperture and a guide boss extending from the flange downwardly into the aperture. At least two cog pins extend downwardly from the guide boss, and a disc is secured to cog pins. The cog pins are so constructed and configured that when the handle is turned the cog pins progressively engage the teeth formed in the rack forcing the second arm to move along the rack. In one very important embodiment, a single first retractor blade is pivotally secured to the first arm for engagement with the sternum of the patient and a single second retractor blade is pivotally secured to the second arm for engagement with the sternum of the patient. The blades and arms are so configured and constructed that, in use, the respective pivotal blade on the respective arm is the sole engagement with respective edge of the patient's sternum. The blade, therefore, is initially aligned with the respective edge of the patient's sternum and, very importantly, remains in alignment during the spreading of the sternum.

The sternal retractor may comprise an atrial retractor comprises an H-shaped mounting rod assembly and a plurality of rods, retractor hooks and rod mounts and connectors connected together to extend between the extended portions of the sternum of a patient to engage thoracic organs in the chest of a patient when the retractor is in use and to permit the surgeon to adapt the retractor to be used in various surgical procedures.

Also, the rack and cog mechanism is, in a highly preferred and important embodiment, so constructed and configured the rack lies adjacent, when in use, to the patient's chest. Very importantly, in this embodiment, the rack is generally arcuately curved in a plane perpendicular to the patient's chest such that the arc of the rack approximates the curvature of the patient's chest. This causes the opposed edges of the sternum to open along path that is curved, generally arcuate, in a plane perpendicular to the backbone of the patient. This permits the rib cage to be opened more naturally without substantial lifting of the respective edges of the rib cage. This results in less trauma to the patent, a very important result not heretofore accomplished in sternal retractors.

BRIEF DESCRIPTION OF THE DRAWINGS

The present invention may be better understood and the advantages will become apparent to those skilled in the art by reference to the accompanying drawings, wherein like reference numerals refer to like elements in the several figures, and wherein.

DESCRIPTION OF THE PREFERRED EMBODIMENTS

Figure 1:
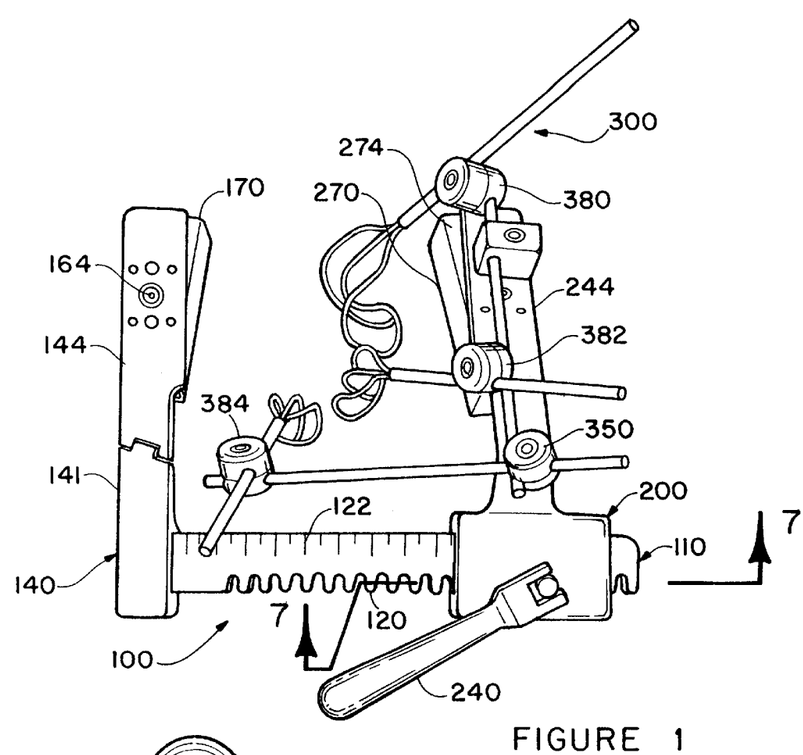
FIG. 1 is a perspective view of the sternal retractor to which the atrial retractor assembly is fastened.

Referring to the drawings wherein like numerals indicate like elements there is shown in FIG. 1 a plan view of the sternal retractor 100 of this invention. The sternal retractor 100 comprises a curved rack 110, having a first end to which is fixed a first arm 140 and a second arm 200 mounted for movement along the length of the rack 110 toward the second end thereof.

Figure 2:
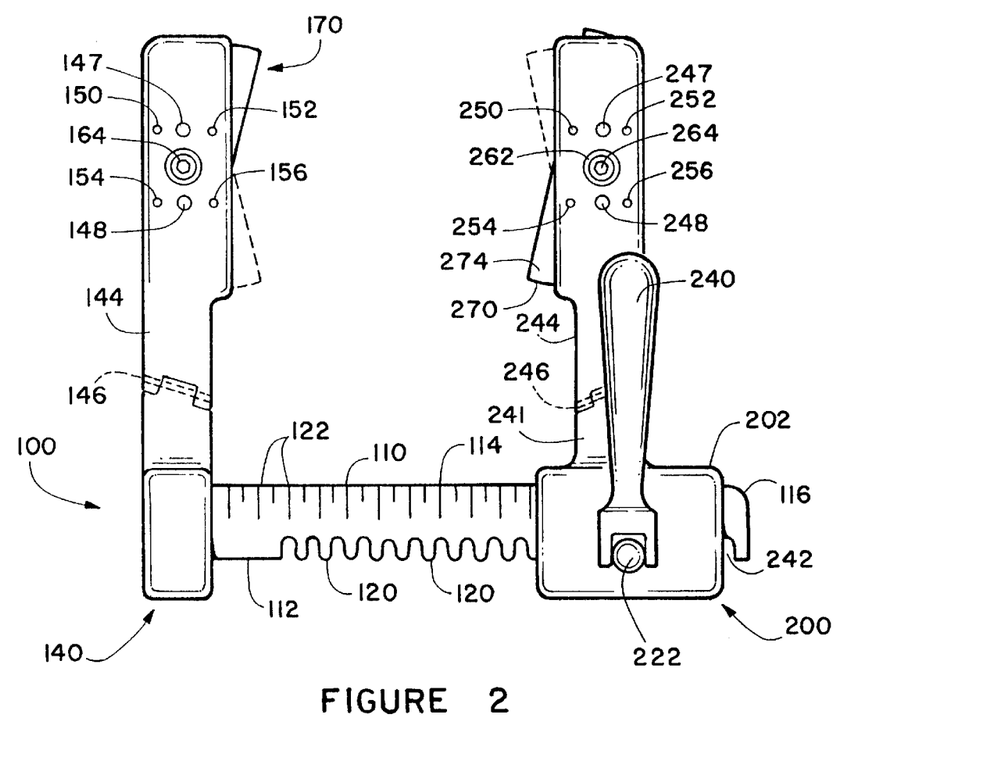
FIG. 2 shows a plan view of the sternal retractor.
Figure 3:
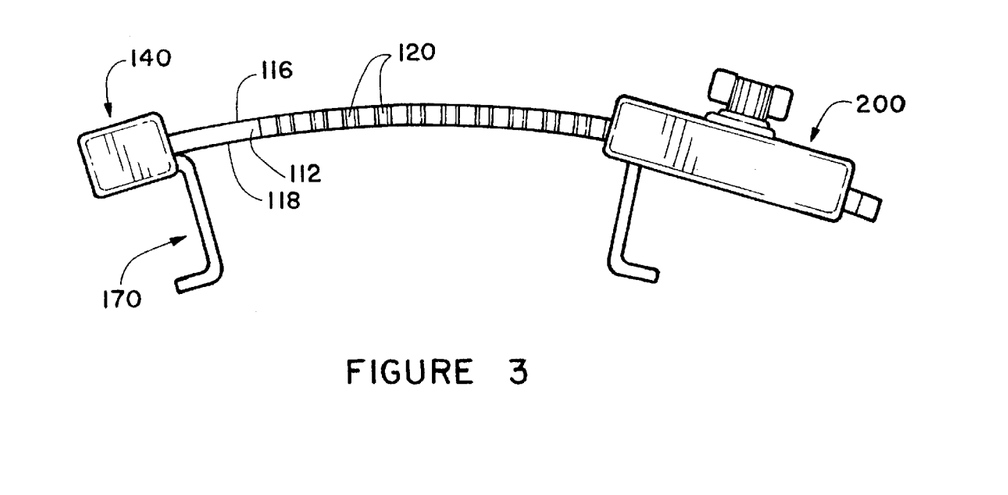
FIG. 3 shows an end view of the sternal retractor shown in FIG. 1.
Figure 4:
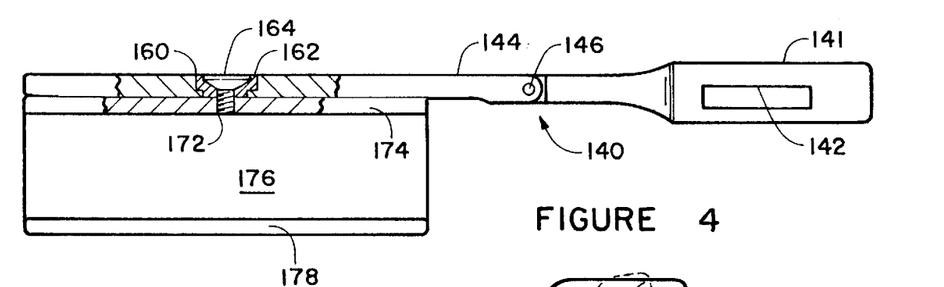
FIG. 4 depicts, in partial cross-section, the first articulated arm of the sternal.
Figure 5:
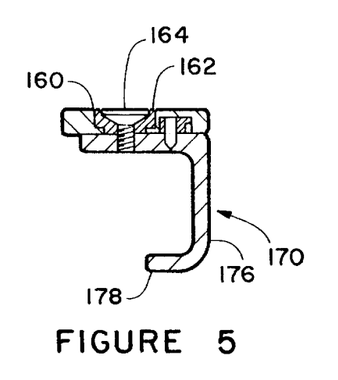
FIG. 5 is a top plan view of the blade assembly of the first articulated arm showing only a portion of the arm, the blade being shown in phantom lines to depict one position thereof.
Figure 6:
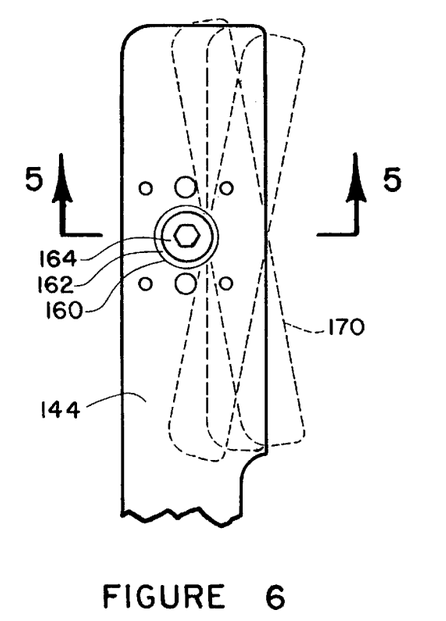
FIG. 6 is a partial cross-section of the sternal retractor blade assembly shown in FIG. 5 taken along line 6—6 in the direction of the arrows with the blade aligned with the arm.

The configuration of the rack 110 is best understood by referring to FIGS. 1 and 2. The rack 110 is an arcuately curved elongate bar that has a rectangular cross-sectional configuration that define first and second edges 112 and 114 and first and second sides 116 and 118, the sides being from about three to about ten times wider than the thickness of the edges. A rectangular bar of about one-eighth to one-fourth inch thick and about one inch to one and a half inch wide is suitable. The rack bar is typically formed of a stainless steel bar having a thickness Th of about ¼ inch, a width W of about 1 inch, and a length L of about 10 inches, all as shown in FIGS. 2 and 3, the thickness of bar being bent, leaving the length and width to define a rectangle, to define an arc having a radius of curvature of from 9 inches to 20 inches. As clearly shown in FIGS. 2 and 3, the sides defining the rectangular sides and the ends of the bar remain rectangular, each end and each side lying in a single plane, whereas the thickness is arcuate. Inherent in the structure just described is that the bar has two sides, one on top of the thickness and one on the bottom of the thickness, as shown in the drawings. The top side, as shown, defines a convex curve Cx, shown in FIG. 3, and a bottom side Cv, also shown in FIG. 3. The bottom concave side Cv rests upon the chest of the patient during use, as clearly shown in FIG. 18. The curvature of the bar and, consequently, of the bottom concave side Cv side, approximates the curvature of the patient's chest from one side to the other, also as clearly shown in FIG. 18. Also as clearly shown in FIG. 18, the tangent T to the convex upper side Cx lies generally perpendicular to the radius or, equivalently, radii R of curvature of the bar. The sides of the bar inherently lie in parallel planes before and after the bar is bent. Likewise, the ends of the bar, indicated by dimension W, also inherently lie in parallel planes. The dimensions are not critical. In general, however, the rack has a width about four times the thickness thereof and a length about ten times the width and a radius of curvature in the thickness dimension of from about nine to about 20 inches. A set of retractors may be provided of varying dimensions and curvature for use in pediatric surgery and on adults of different sizes. The rack has a multiplicity of teeth, indicated generally at 120 formed in the bar along the first edge 112 for receiving a gear as will be described. The teeth 120 extend from a short distance from the first arm 140 on the first end of the rack to the second end of the rack to permit the second arm 200 to be fitted onto the rack from the second end and to move along the greater part of the length of the rack. The first side 116 of the rack bar has formed therein or printed thereon distance measuring indecia 122 so disposed on the bar as to indicate the distance the sternum is spread during use of the sternal retractor.

Reference is made now to FIGS. 1 through 6. The first arm 140 comprises a mount 141 which has a generally rectangular passage 142 formed therethrough to accept the rack 110. A first articulated arm 144 is pivotally secured to the mount 141 by means of a hinge pin 146. The first articulated arm 144 has formed in it one or more threaded apertures 147 and 148 and one or more guide apertures 150, 152, 154 and 156, best shown in FIGS. 2, 4, 5 and 6, to permit atrial retractors to be attached, as will be described. Referring momentarily FIGS. 4, 5 and 6 in particular, it will be seen that the first articulated arm 141 also has a stepped aperture 160 formed therethrough that receives a compressible bearing 162 which in turn receives a securing bolt 164 for the first retractor blade 170 by means of threaded aperture 174 to the first articulated arm. The first retractor blade 170 is an elongate generally U-shaped body that comprises a mounting plate portion 172, in which the threaded aperture 174 is formed, a downward extender plate 176 extending generally perpendicularly from one edge of the mounting plate portion 174 to a bottom edge from which an engaging blade portion 178 extends generally perpendicularly to lie in a plane generally parallel to the plane in which the mounting plate 174 lies and extending from the extender plate in the same direction as the mounting plate extends from the extender plate.

One important feature of this invention is the construction and arrangement of the articulated arms with the blades secured thereto in such a manner as to permit the blades to self-adjust to the angle at which the sternum lies in the patient when the retractor is in use. The bearing 162 permits the blade 170 to pivot relative to the arm 141, the pivoted position being shown in phantom lines in the figures, but retains the blade in any given position in the absence of force causing the self-adjusting pivoting action.

Referring now to FIGS. 1, 2, 3 and FIGS. 6 and 7, it will be noted that the second arm is substantially a mirror image of the first arm, except that the second arm includes a cog mechanism to permit the second arm to be moved along the rack. The second articulated arm 244 is a nearly identical mirror image of the first articulated arm 144.

Figures 7, 8:
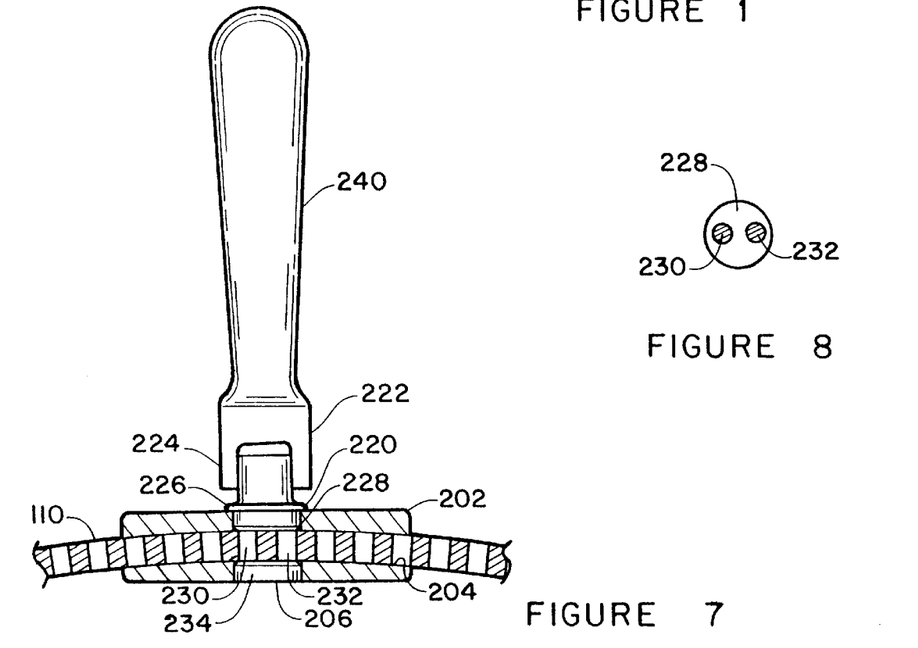
FIG. 7 is a partial cross-sectional view of the rack and cog structure taken substantially along lines 7—7 shown in FIG. 1 in the direction of the arrows.
FIG. 8 is an end view of the cog driver shown in FIG. 7.

The second arm 200 comprises a mounting body 202 through which is formed a passage having a generally rectangular cross-section to receive the rack, the passage being sufficiently larger than the rack to permit the body to slide along the rack. The body 202 may be manufactured in any desired manner, such as chemical etch machining, etc., or may be made in pieces and assembled. The passage need not be arcuate if it is made enough wider than the rack to accommodate the arcuitivity of the rack. The body also has a aperture 206 formed through it perpendicular to the passage to receive the cog mechanism 220 used to move the body along the rack.

Figure 18:
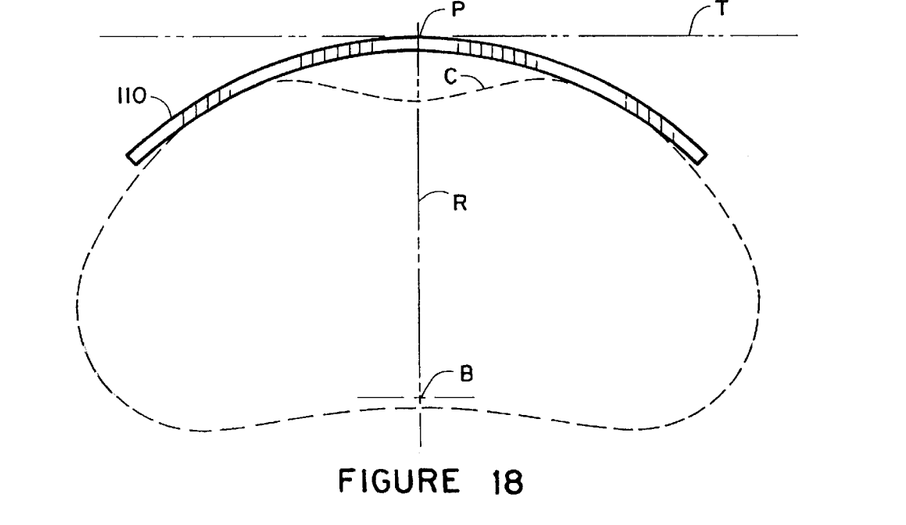
FIG. 18 depicts in very simplified form a side elevational view of the rack, without showing the teeth or other structures, resting on the chest of the patient, the overall outline of the torso of the patient including the chest portion being depicted in dashed lines.

The configuration of the rack, as part of the overall combination, is an important feature. The importance of the curvature of the rack in its thickness dimension will be apparent from the following discussion in which reference is made to FIG. 18. FIG. 18 depicts in very simplified form a side elevational view of the rack 110, without showing the teeth or other structures, resting on the chest C of the patient, the overall outline of the torso of the patient including the chest portion being depicted in dashed lines. The rack, as noted previously, is curved in its thickness dimension in a generally arcuate configuration. The depiction in FIG. 18 for simplicity of illustration shows a circular arc having a radius of curvature R from a single center B, but other than circular arcs may be used. For example an elliptical arc may be used. In either case, the radius or radii of the arc defined by the rack in its thickness dimension extend substantially perpendicular to the backbone of the patent, when the device is in use. The arc of the rack, as depicted in FIG. 18, lies in an imaginary plane that extends through the thickness of the rack, i.e. the arc lies in or parallel to the plane of the paper on which the drawing is depicted. The plane in which the arc lies is perpendicular to a line drawn across the width to the rack through a point P perpendicular to the plane of the drawing paper. The generally arcuate configuration may also be described as defining an imaginary tangent line T extending longitudinally parallel to a side edge of the rack.

The cog mechanism 220 comprises an upstanding pivot mount 222 for receiving an actuating handle 240, the actuating handle 240 being connected to the pivot mount by means of a pivot pin 224. The pivot mount 222 extends upwardly, as the retractor is disposed in use, from a flange 226 that rests against the surface of the body 202 circumferentially adjacent the aperture 206. A guide boss 228 extends down into the aperture 206 from which extends two cog pins 230 and 232 secured in a disc 234 at the lower end. As will be apparent from FIG. 2 and 6, when the handle 240 is turned, the cog pins 230 and 232 engage, progressively, the teeth 120 in the rack 120 forcing the second arm 200 to move along the rack.

The second arm 200 comprises a mount 241 which has a rectangular passage 242 formed therethrough to accept the rack 110. A second articulated arm 244 is pivotally secured to the mount 241 by means of a pin 246. The second articulated arm 244 has formed in it one or more threaded apertures 247 and 246 and one or more guide apertures 248, 250, 252, 254 and 256 to permit atrial retractors to be attached. The second articulated arm 244 also has a stepped aperture formed therethrough that receives a compressible bearing 262 which in turn receives a securing bolt 264 for the second retractor blade 270 by means of a threaded aperture 272 to the second articulated arm. The second retractor blade 270 is an elongate generally U-shaped body that comprises a mounting plate portion 274, in which the threaded aperture 272 is formed, a downward extender plate 276 extending generally perpendicularly from one edge of the mounting plate portion 274 to a bottom edge from which an engaging blade portion 278 extends generally perpendicularly to lie in a plane generally parallel to the plane in which the mounting plate 274 lies and extending from the extender plate in the same direction as the mounting plate extends from the extender plate.

In use, the surgeon makes a sternal midline incision and places the sternal retractor over the sternum with the two arms adjacent each other, inserting the blades in the sternal incision with the blades extending outwardly. The handle 240 is turned, operating the cog mechanism and driving the second arm to the right, as depicted in FIG. 1, the blades spreading the two sternal portions apart exposing the thoracic organs. The handle may be positioned generally horizontally away from the operating opening.

The sternal retractor may be used alone or with other retracting devices.

Figure 9:
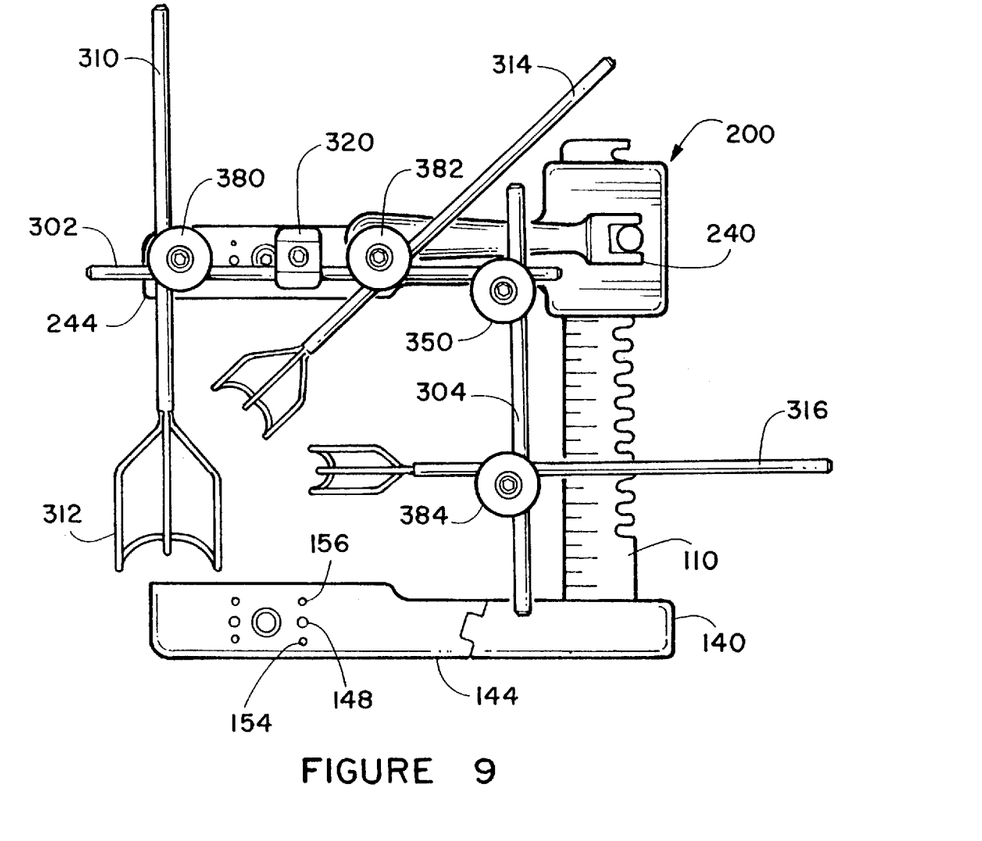
FIG. 9 shows a plan view of the sternal retractor with the atrial retracting elements attached.
Figure 10:
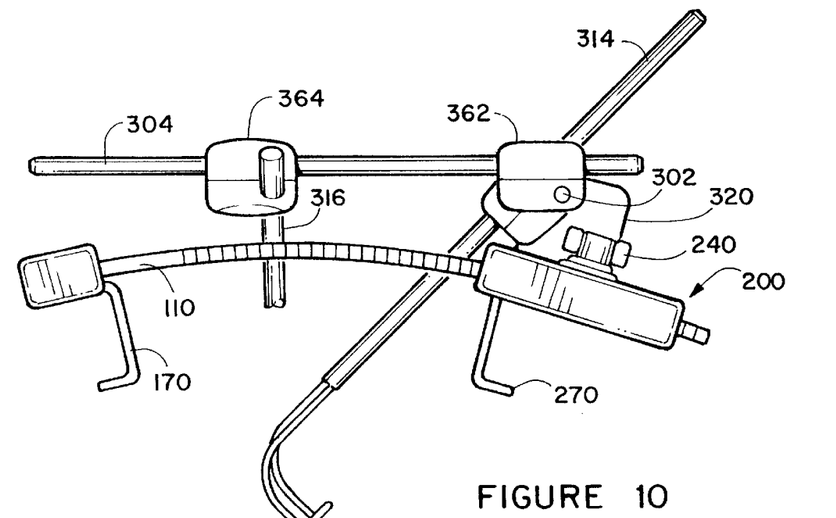
FIG. 10 shows an end view of the sternal retractor with two of the atrial retracting elements attached.

In performing various surgical procedures on the heart the sternal retractor is used in association with an atrial retractor assembly shown in FIGS. 9 through 12. Referring first to FIGS. 9 and 10, it will be seen that the atrial retractor 300 comprises a plurality of rods, retractor hooks and rod mounts and connectors. It will be apparent that any number of rods and any number of retractor hooks may be connected together in any of an infinite number of configurations to permit the surgeon to adapt the retractor to be used in various surgical procedures.

Figure 11:
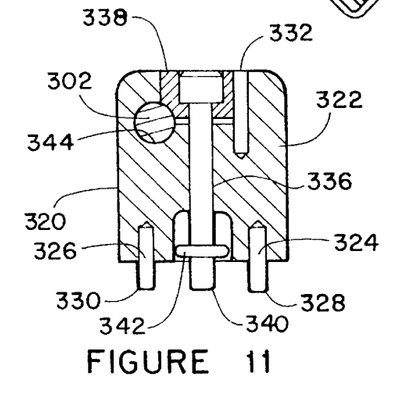
FIG. 11 shows a cross-section of the pillar clamp.

In the exemplary configuration shown in FIG. 9, and also in FIG. 10 with one retractor hook assembly omitted, a rod 302 is secured to the second articulated arm 244 by means of a pillar clamp 320. The pillar clamp 320 is depicted in FIG. 11 to which reference is now made. The pillar clamp comprises a body 322 having a flat bottom into which apertures 324 and 326 are drilled or otherwise formed. Guide pins 328 and 330 are received in the respective apertures and, in use, extend down in guide apertures 254 and 256 in the second articulated arm 244, previously described but not shown in FIG. 9. The block 322 has another guide aperture 332 for receiving an additional guide pin if it is desired to stack two blocks together. A passage 334 is configured and dimensioned to receive rod 302. A three-stepped diameter passage 336 extends vertically through the block and receives a stainless steel bearing 338 which, in turn, receives a securing bolt 340 that extends down through the block, being maintained in the passage by a keeper 342, and is screwed into threaded aperture 248, shown in FIG. 2, in the second articulated arm 244.

Figure 12:
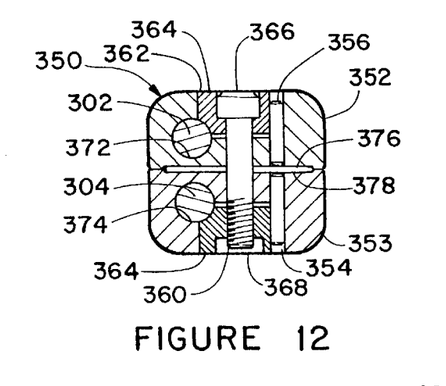
FIG. 12 shows a cross-section of the ball clamp.
Figure 13:
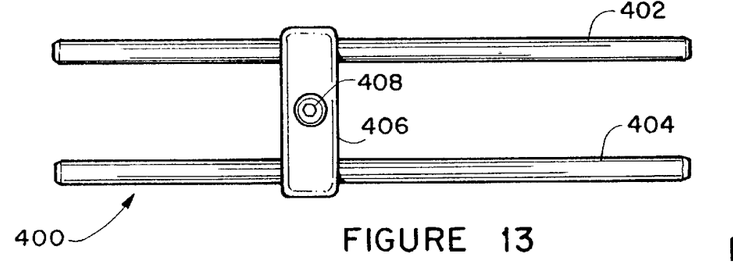
FIG. 13 is a top, plan view of the "H", mounting rod assembly that provides greater flexibility for positioning atrial retracting rods and hooks.
Figure 14:
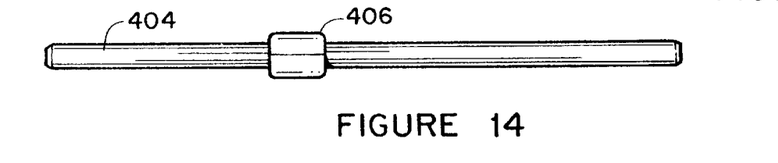
FIG. 14 is a side, elevational view of the "H" mounting rod assembly that provides greater flexibility for positioning atrial retracting rods and hooks.
Figure 15:
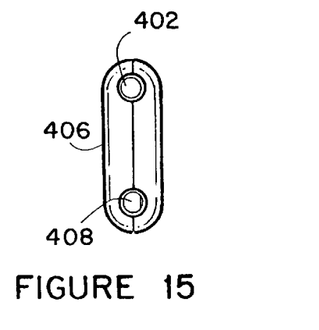
FIG. 15 is an end view of the "H", mounting rod assembly that provides greater flexibility for positioning atrial retracting rods and hooks.

The rod 302 is connected to a second rod 304 by a ball clamp 350, which is shown in FIG. 12 shown rotated so that the rods 302 and 304 are both visible and lying generally parallel to each other, to which reference is now made. The ball clamp 350 comprises two thick discoid blocks 352 and 353 having formed therein, respectively, guide apertures 354 and 356 for receiving guide pins to lock the discoid blocks 352 and 353 in a specific angular relationship if a fixed angle is desired. Several guide apertures may be provided. A triple-diameter stepped passage 360 extends through the axes of the blocks 352 and 353 and receive a grommet 364 in the enlarged top portion 362 which, in turn, receives the bolt 366 which extends axially through the discoid blocks and is threadably received in grommet 368 in the enlarged bottom opening of the ball clamp. Passages 372 and 374 extend to the side of and perpendicular to the axes in the respective discoid blocks and intersect the upper and lower enlarged portions 362 and 368 and portions of the grommets 364 and 370. It will now be understood that when the bolt 366 is tightened, it locks the two discoid blocks together and also locks the rods, e.g. 302 and 304, in the passages 354 and 352 respectively and, if no guide pins are used, fixes the angular relationship between the rods.

The ball clamps can be used to connect any desired number of retractor hooks as part of the atrial retractor 300. In FIG. 9, for example, retractor hook 310 is connected to rod 302 with the hook portion 312 extending sharply downwardly into the surgical opening. Hooks 314 and 316 respectively are secured to rod 302 and rod 304 respectively. It will be apparent that complete freedom of position in the lateral and vertical planes is easily accomplished using the atrial retractor of this invention in association with the sternal retractor.

Reference is now made to FIGS. 13 through 17. Another facet of the invention is the incorporation into the an atrial retractor (300) of an H-shaped mounting rod assembly (400) to which one or a plurality of rods, retractor hooks and rod mounts and connectors may be connected together to extend between the extended portions of the sternum of a patient to engage thoracic organs in the chest of a patient when the retractor is in use and to permit the surgeon to adapt the retractor to be used in various surgical procedures. The H-shaped mounting rod assembly, referred to for simplicity as the H-assembly, comprises a pair of rods of approximately the same length secured at approximately the center of the rods in spaced apart relationship. The rods 402 and 404 are, in this invention, from about ⅛th to about ⅜ths inch in diameter, but diametrical or other dimensions are not critical. A cross-clamp 406, with a clamping screw or fastener 408, may be used to releasably secure the rods rigidly at a spacing of from about one to about 3 inches; however, a tight press-fit of the rods in apertures in the cross-clamp is a preferred method of connection. The method of connection and the dimensions are not critical.

Figure 16:
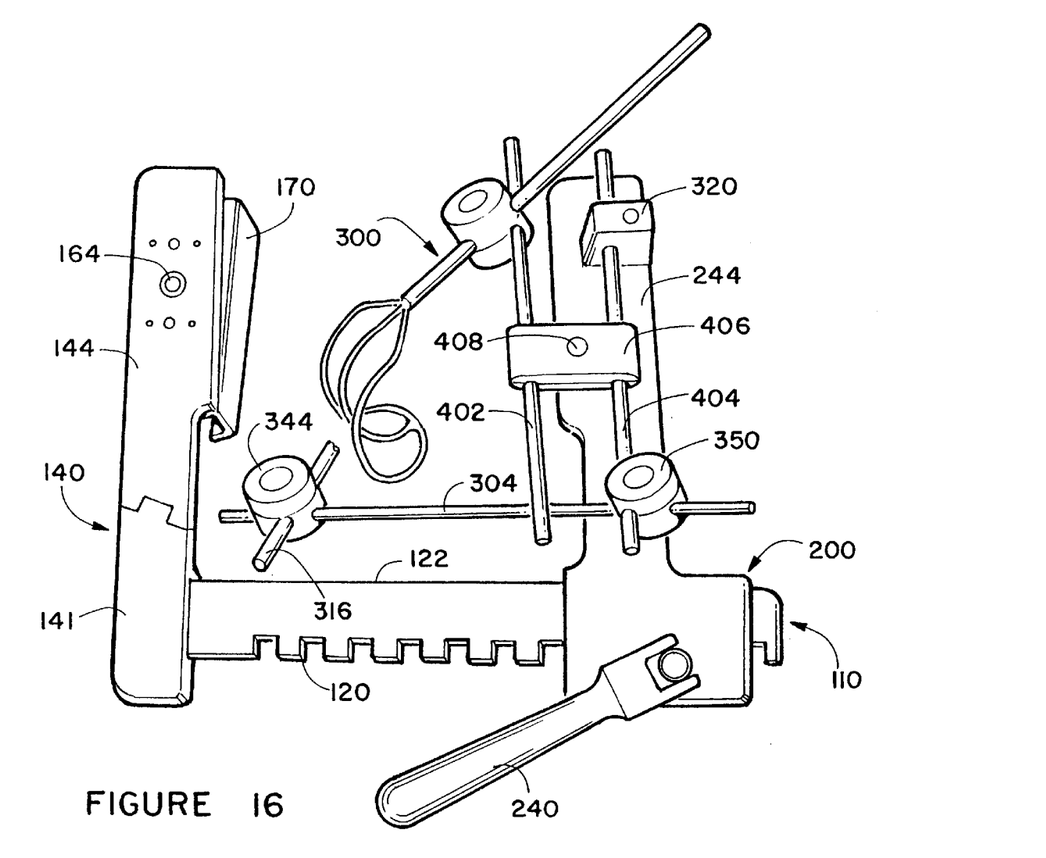
FIG. 16 is a perspective view, taken approximately downward as the device would be oriented in use, of the sternal retractor to which the "H" mounting bar assembly and the atrial retractor assembly is fastened, portions of the structure being omitted for clarity.
Figure 17:
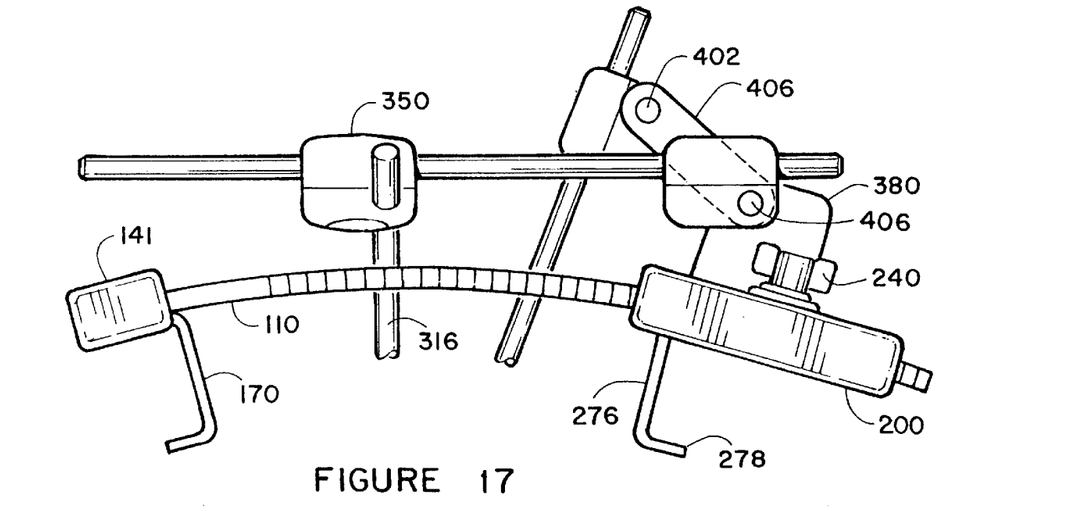
FIG. 17 is a perspective view, taken approximately perpendicular to the view of FIG. 16, of the sternal retractor to which the "H" mounting bar assembly and the atrial retractor assembly is fastened, portions of the structure being omitted for clarity.

As shown in FIGS. 16 and 17, the rods 402 and 404 of the H-assembly permit an additional, and very important, degree of adjustability. The surgeon can quickly and easily reposition an atrial hook, or other rod clamped to the atrial clamp assembly, simply by rotating one or both of the rods 406 and/or 404 in the cross-clamp 406.

The invention as described has several important advantages over prior art devices. For example, adequate exposure of the mitral or tricuspid valve is easily accomplished using two or three adjustable retractor hooks in connection with sternal retractor. The retractors can be adjusted to position the retractor hooks in virtually any spacial relationship relative to each other and to the sternal retractor, being independently adjustable as to horizontal position, angle and length. The atrial retractor is easily attached to and detached from the sternal retractor to permit full access to the thoracic organs. The sternal blades pivot to provide uniform force on the sternum and more natural opening of the chest. The curved rack reduces surgeon interference and the measuring scale permits precise, predetermined opening and prevents over-extension of the sternum.

Industrial Application

This invention is useful in the health and surgical fields.
What is claimed is:

1. A sternal retractor (100) comprising a curved rack (110) constructed to define along, at least a portion of the length thereof a plurality of teeth and having a first end and a second end, a first arm (140) attached adjacent the first end, a second arm (200) mounted for movement along the length of the rack between the first and second ends, the first arm (140) comprising a mount (141) which has a rectangular passage (142) formed there through to accept the rack (110), a first articulated arm (144) pivotally secured to the mount (141), the second arm (200) comprising a mounting body (202) through which is formed a passage (204) having a generally rectangular cross-section to receive the rack, the passage being sufficiently larger than the rack to permit the body to slide along the rack, a cog mechanism (220) constructed and configured to force the second arm (200) to move alone the rack upon operation of the cog mechanism, and only one, single first retractor blade (170) pivotally secured to the first arm for engagement with the sternum of the patient and only one ingle second retractor blade (270) pivotally secured to the second arm for engagement with the sternum of the patient, the blades and arms being so configured and constructed that, in use, the respective blade is the sole engagement with respective edges of the patient's sternum to be separated to pivotally align with said respective edges of the patient's sternum for applying opening force evenly along the respective blade only to that portion of the respective edges of the sternum engaged by the single blade, and wherein the rack has a length (L), a width (W) and a thickness (Th) and is curved in the thickness dimension of the rack to define a convex side (Cx) and a concave side (Cv) and is so constructed and configured that, in use, the concave side (Cv) lies on the patient's chest and the tangent (T) of the convex side (Cx) is perpendicular to the radius of curvature (R) of the rack, which radius approximates the curvature of the patient's chest, for thereby separating the opposed edges of the sternum along a curved path that lies in the plane defined by the radius (R) and perpendicular to the tangent (T).

2. A sternal retractor (100) comprising a curved rack (110) constructed to define along at least a portion of the length thereof a plurality of teeth and having a first end and a second end, a first arm (140) attached adjacent the first end, a second arm (200) mounted for movement along the length of the rack between the first and second ends, the first arm (140) comprising a mount (141) which has a rectangular passage (142) formed there through to accept the rack (110), a first articulated arm (144) pivotally secured to the mount (141), the second arm (200) comprising a mounting body (202) through which is formed a passage (204) having a generally rectangular cross-section to receive the rack, the passage being sufficiently larger than the rack to permit the body to slide along the rack, a cog mechanism (220) constructed and configured to force the second arm (200) to move along the rack upon operation of the cog mechanism, and only one, single first retractor blade (170) pivotally secured to the first arm for engagement with the sternum of the patient and only one ingle second retractor blade (270) pivotally secured to the second arm for engagement with the sternum of the patient, the blades and arms being so configured and constructed that, in use, the respective blade is the sole engagement with respective edges of the patient's sternum to be separated to pivotally align with said respective edges of the patient's sternum for applying opening force evenly along the respective blade only to that portion of the respective edges of the sternum engaged by the single blade, and further comprising an atrial retractor (300) connected to an arm of the sternal retractor, the atrial retractor comprising an H-shaped mounting rod assembly (400) comprising two elongate rods mounted in space parallel relationship by a clamp proximate the center of the rods, one of said elongate rods being mounted on an arm and a plurality of rods, retractor hooks and rod mounts and connectors connected together to extend between the extended portions of the sternum of a patient to engage thoracic organs in the chest of a patient when the retractor is in use and to permit the surgeon to adapt the retractor to be used in various surgical procedures.

3. The sternal retractor of claim 2 wherein the rack has a length (L), a width (W) and a thickness (Th) and is curved in the thickness dimension of the rack to thereby inherently define a convex side (Cx) inherently defining a tangent (T), a concave side (Cv) of length (L) and width (W) and is so constructed and configured that, in use, the curvature approximates the curvature of the patient's chest, the concave side (Cv) resting on the patient's chest for thereby separating the opposed edges of the sternum to open along a curved path that lies in the plane defined by the radius (R) and tangent (T).

4. A sternal retractor (100) comprising an elongate rack (110) having a length (L), a width (W) and a thickness (Th) that is curved in the thickness dimension of the rack to define a convex side (Cx), having a tangent (T), and a concave side (Cv) and a first end and a second end, a first arm (140) attached adjacent the first end, a second arm (200) mounted for movement along the length of the rack between the first and second ends, first and second retractor blades (170,270) mounted, respectively, on the first and second arms for engaging opposed edges of the sternum of the patient when in use, and a cog mechanism (220) for forcing the second arm (200) to move along the rack while the retractor blades are so engaged for spreading the edges of the sternum apart, the rack and cog mechanism being so constructed that the concave side Cv of the rack lies, when in use, adjacent the patient's chest, the radius of curvature (R) of the rack lying in a plane generally perpendicular to the patient's backbone such that the arc of the rack approximates the curvature of the patient's chest, for thereby separating the opposed edges of the sternum along a curved path in a plane defined generally by the radius of curvature (R) of and a tangent (T) to the rack.

5. The sternal retractor of claim 4 wherein the radius of curvature of the rack is from about 9 to 20 inches.

6. The sternal retractor of claim 5 wherein the retractor blades comprise a single first retractor blade (170) pivotally secured to the first arm for engagement with the sternum of the patient and a single second retractor blade (270) pivotally secured to the second arm for engagement with the sternum of the patient, the blades and arms being so configured and constructed that, in use, the respective blade is the sole engagement with respective edges of the patient's sternum to be separated and to pivotally align with said respective edges of the patient's sternum.

7. The sternal retractor of claim 6 further comprising an atrial retractor (300) comprising an H-shaped mounting rod assembly (400) comprising two elongate rods mounted in space parallel relationship by a clamp proximate the center of the rods, one of said elongate rods being mounted on an arm and a plurality of rods, retractor hooks and rod mounts and connectors connected together to extend between the extended portions of the sternum of a patient to engage thoracic organs in the chest of a patient when the retractor is in use and to permit the surgeon to adapt the retractor to be used in various surgical procedures.

8. The sternal retractor of claim 4 wherein the retractor blades comprise a single first retractor blade (170) pivotally secured to the first arm for engagement with the sternum of the patient and a single second retractor blade (270) pivotally secured to the second arm for engagement with the sternum of the patient, the blades and arms being so configured and constructed that, in use, the respective blade is the sole engagement with respective edges of the patient's sternum to be separated and to pivotally align with said respective edges of the patient's sternum.

9. The sternal retractor of claim 8 further comprising an atrial retractor (300) comprising an H-shaped mounting rod assembly (400) comprising two elongate rods mounted in space parallel relationship by a clamp proximate the center of the rods, one of said elongate rods being mounted on an arm and a plurality of rods, retractor hooks and rod mounts and connectors connected together to extend between the extended portions of the sternum of a patient to engage thoracic organs in the chest of a patient when the retractor is in use and to permit the surgeon to adapt the retractor to be used in various surgical procedures.

10. A sternal retractor (100) comprising an elongate rack (110) having a generally rectangular cross section and a first end and a second end, a first arm (140) attached adjacent the first end, a second arm (200) mounted for movement along the length of the rack between the first and second ends, first and second retractor blades (170,270) mounted, respectively, on the first and second arms for engaging opposed edges of the sternum of the patient when in use, a cog mechanism (220) for forcing the second arm (200) to move along the rack while the retractor blades are so engaged for spreading the edges of the sternum apart, and an atrial retractor (300) comprising an H-shaped mounting rod assembly (400) comprising two elongate rods mounted in space parallel relationship by a clamp proximate the center of the rods, one of said elongate rods being mounted on an arm and a plurality of rods, retractor hooks and rod mounts and connectors connected together to extend between the extended portions of the sternum of a patient to engage thoracic organs in the chest of a patient when the retractor is in use and to permit the surgeon to adapt the retractor to be used in various surgical procedures.

11. The sternal retractor of claim 10 wherein the atrial retractor further comprises a ball clamp releasably interconnecting a plurality of rods together, said clamp being connected to the sternal retractor and comprising first and second discoid blocks, each of said blocks having an axis, each of said blocks having formed therein a stepped passage extending through the axis of the block, a grommet in the stepped passage of each block, a bolt extending axially through the discoid blocks and the grommet in the stepped passage of one of said blocks and being threadably received in the grommet in the stepped passage of the other of said blocks, each of said blocks defining a rod passage beside and generally perpendicular to the stepped passage for receiving rods to be locked in position relative to each other, said respective rod passages intersecting in the respective blocks the stepped passage in said block and at least a portion of the grommets in said stepped passage, the blocks and respective grommets being so constructed and configured that when the bolt is tightened the two discoid blocks are locked together and the rods in a fixed orientation relative to each other.

12. The sternal retractor of claim 11 wherein each of the blocks of the ball clamp has formed therein respectively a guide aperture for receiving a guide pin for selectively locking the blocks a specific angular relationship.

13. A sternal retractor (100) comprising curved rack (110) configured and constructed to define teeth along a portion of the length thereof and having a first and second end, a first arm (140) attached adjacent the first end, a second arm (200) mounted for movement along the length of the rack between the first and second ends, the first arm (140) comprising a mount (141) which has a rectangular passage (142) formed there through to accept the rack (110), a first articulated arm (144) pivotally secured to the mount (141), the second arm (200) comprising a mounting body (202) through which is formed a passage (204) having a generally rectangular cross-section to receive the rack, the passage being sufficiently larger than the rack to permit the body to slide along the rack, an aperture (206) formed through the body (202) perpendicular to the passage (204), and a cog mechanism (220) extending through the aperture (206), the cog mechanism comprising an upstanding pivot mount (222), an actuating handle (240) connected thereto, a flange (226) supporting the pivot mount and resting against the surface of the body (202) circumferentially adjacent the aperture (206), a guide boss (228) extending from the flange downwardly into the aperture (206), at least two cog pins (230, 232) extending downwardly from the guide boss, and a disc (234) secured to cog pins, the cog pins being so constructed and configured that when the handle (240) is turned the cog pins progressively engage the teeth (120) formed in the rack (110) forcing the second arm (200) to move along the rack, the first and second articulated arms having formed therein at least one threaded aperture and at least one guide aperture, a single, sole first retractor blade (170) being pivotally secured to the first arm and a single, sole second retractor blade (270) being pivotally secured to the second arm, the blades and arms being so configured and constructed that, in use, the respective pivotally mounted blades engage the patient's sternum and pivot to be aligned with said sternum and to remain in alignment with the sternum as the sternum is separated.

14. A ball clamp for releasably interconnecting two rods together comprising first and second discoid blocks, each of said blocks having an axis, each of said blocks having formed therein a stepped passage extending through the axis of the block, a grommet in the stepped passage of each block, a bolt extending axially through the discoid blocks and the grommet in the stepped passage of one of said blocks and being threadably received in the grommet in the stepped passage of the other of said blocks, each of said blocks defining a rod passage beside and generally perpendicular to the stepped passage for receiving rods to be locked in position relative to each other, said respective rod passages intersecting in the respective blocks the stepped passage in said block and at least a portion of the grommets in said stepped passage, the blocks and grommets being so constructed and configured that when the bolt is tightened the two discoid blocks are locked together and the rods are locked in a fixed orientation relative to each other.

15. The ball clamp of claim 14 wherein each of the blocks has formed therein respectively a guide aperture for receiving a guide pin for selectively locking the blocks in a specific angular relationship.

* * * * *